US008859779B2

(12) United States Patent
Nolan et al.

(10) Patent No.: US 8,859,779 B2
(45) Date of Patent: Oct. 14, 2014

(54) CATALYST COMPLEX WITH CARBENE LIGAND

(71) Applicant: Materia, Inc., Pasadena, CA (US)

(72) Inventors: Steven P. Nolan, St. Andrews (GB); Jinkun Huang, Thousand Oaks, CA (US)

(73) Assignee: Materia, Inc., Pasadena, CA (US)

( * ) Notice: Subject to any disclaimer, the term of this patent is extended or adjusted under 35 U.S.C. 154(b) by 0 days.

(21) Appl. No.: 13/750,265

(22) Filed: Jan. 25, 2013

(65) Prior Publication Data

US 2013/0261296 A1 Oct. 3, 2013

Related U.S. Application Data

(63) Continuation of application No. 13/041,573, filed on Mar. 7, 2011, now abandoned, which is a continuation (Continued)

(51) Int. Cl.

| C07F 15/00 | (2006.01) |
|---|---|
| C07C 67/30 | (2006.01) |
| C07D 207/46 | (2006.01) |
| B01J 31/00 | (2006.01) |
| B01J 31/24 | (2006.01) |
| B01J 31/22 | (2006.01) |
| C07D 223/04 | (2006.01) |
| C07C 6/04 | (2006.01) |
| C07D 313/00 | (2006.01) |
| C07D 225/02 | (2006.01) |
| C07D 498/04 | (2006.01) |

(52) U.S. Cl.
CPC .............. C07F 15/00 (2013.01); *B01J 2231/54* (2013.01); B01J 31/2404 (2013.01); *B01J 2531/825* (2013.01); *B01J 2231/543* (2013.01); B01J 31/2273 (2013.01); C07D 223/04 (2013.01); C07C 6/04 (2013.01); C07F 15/002 (2013.01); C07C 67/30 (2013.01); C07D 207/46 (2013.01); C07D 313/00 (2013.01); *B01J 31/2265* (2013.01); C07F 15/0046 (2013.01); C07D 225/02 (2013.01); *B01J 31/2295* (2013.01); C07D 498/04 (2013.01); *B01J 31/2278* (2013.01); *B01J 2531/821* (2013.01)
USPC ........... 548/101; 585/350; 585/366; 585/643; 556/21; 556/136; 556/137; 548/103; 502/152; 502/162

(58) Field of Classification Search
USPC ............. 502/152, 162; 548/101, 103; 556/21, 556/136, 137; 585/350, 366, 643
See application file for complete search history.

(56) References Cited

U.S. PATENT DOCUMENTS

| 4,681,956 A | 7/1987 | Schrock |
|---|---|---|
| 5,077,414 A | 12/1991 | Arduengo, III |

(Continued)

FOREIGN PATENT DOCUMENTS

| DE | 19610908 | 9/1997 |
|---|---|---|
| DE | 19815275 | 10/1999 |

(Continued)

OTHER PUBLICATIONS

Ackermann, L., et al. (1999). "Ruthenium Carbene Complexes with Imidazolin-2-ylidene Ligands Allow the Formation of Tetrasubstituted Cycloalkenes by RCM," Tetrahedron Letters 40:4787-4790.

(Continued)

*Primary Examiner* — Porfirio Nazario Gonzalez
(74) *Attorney, Agent, or Firm* — J.A. Lindeman & Co., PLLC

(57) ABSTRACT

Catalytic complexes including a metal atom having anionic ligands, at least one nucleophilic carbene ligand, and an alkylidene, vinylidene, or allenylidene ligand. The complexes are highly stable to air, moisture and thermal degradation. The complexes are designed to efficiently carry out a variety of olefin metathesis reactions.

22 Claims, 6 Drawing Sheets

Related U.S. Application Data of application No. 12/622,225, filed on Nov. 19, 2009, now Pat. No. 7,902,389, which is a continuation of application No. 09/392,869, filed on Sep. 9, 1999, now Pat. No. 7,622,590.

(60) Provisional application No. 60/115,358, filed on Jan. 8, 1999, provisional application No. 60/099,722, filed on Sep. 10, 1998.

(56) References Cited

U.S. PATENT DOCUMENTS

| | | | |
|---|---|---|---|
| 5,146,033 | A | 9/1992 | Schrock et al. |
| 5,182,405 | A | 1/1993 | Arduengo, III |
| 5,312,940 | A | 5/1994 | Grubbs et al. |
| 5,342,909 | A | 8/1994 | Grubbs et al. |
| 5,710,298 | A | 1/1998 | Grubbs et al. |
| 5,728,785 | A | 3/1998 | Grubbs et al. |
| 5,728,839 | A | 3/1998 | Herrmann et al. |
| 5,728,917 | A | 3/1998 | Grubbs et al. |
| 5,750,815 | A | 5/1998 | Grubbs et al. |
| 5,831,108 | A | 11/1998 | Grubbs et al. |
| 5,917,071 | A | 6/1999 | Grubbs et al. |
| 5,932,664 | A | 8/1999 | Chen et al. |
| 5,969,170 | A | 10/1999 | Grubbs et al. |
| 5,977,393 | A | 11/1999 | Grubbs et al. |
| 6,025,496 | A | 2/2000 | Herrmann et al. |
| 6,048,993 | A | 4/2000 | Grubbs et al. |
| 6,077,805 | A | 6/2000 | Van Der Schaaf et al. |
| 6,107,420 | A | 8/2000 | Grubbs et al. |
| 6,111,121 | A | 8/2000 | Grubbs et al. |
| 6,426,419 | B1 | 7/2002 | Grubbs et al. |
| 6,635,768 | B1 | 10/2003 | Herrmann et al. |
| 7,294,717 | B2 | 11/2007 | Herrmann et al. |
| 7,329,758 | B1 | 2/2008 | Grubbs et al. |
| 7,378,528 | B2 | 5/2008 | Herrmann et al. |
| 7,622,590 | B1 | 11/2009 | Nolan et al. |
| 7,683,180 | B2 | 3/2010 | Grubbs et al. |
| 7,902,389 | B2 * | 3/2011 | Nolan et al. ............ 556/21 |
| 2008/0132708 | A1 | 6/2008 | Grubbs et al. |
| 2008/0207911 | A1 | 8/2008 | Herrmann et al. |

FOREIGN PATENT DOCUMENTS

| | | |
|---|---|---|
| EP | 0921129 | 6/1999 |
| EP | 1197509 | 4/2002 |
| JP | 2000212192 A | 8/2000 |
| WO | WO 9604289 A1 | 2/1996 |
| WO | WO 9706185 | 2/1997 |
| WO | WO 9720865 | 6/1997 |
| WO | WO 9729135 | 8/1997 |
| WO | WO 9951344 | 10/1999 |
| WO | WO 0071544 A2 | 11/2000 |
| WO | WO 0073366 A1 | 12/2000 |

OTHER PUBLICATIONS

Arduengo, III et al., "Electronic Stabilization of Nucleophilic Carbenes," Journal of the American Chemical Society, Jul. 1, 1992, vol. 114, No. 14, 5530-5534.

Demonceau, A. et al. (1997). "Novel Ruthenium-Based Catalyst Systems for the Ring-Opening Metathesis Polymerization of Low-Strain Cyclic Olefins," Macromolecules 30{11 ):3127-3136.

Collins, T.J. et al. {1976). "Cyclic Transition-Metal Carbene Complexes from Ring-Closing Reactions on the pi-bound Substrates Carbon Disulfide and Carbon Diselenide. 1 ,3-Dithiolan-2-ylidene and 1 ,3-Diselenolan-2-ylidene Complexes of Ruthenium (II) and Osmium(ll)," Database Accession No. 84:135795 and J. Organomet. Chem. 107(3):C37-C39.

Dias et al., "Well-Defined Ruthenium Olefin Metathesis Catalysts: Mechanism and Activity," Journal of the American Chemical Society, Apr. 30, 1997, vol. 119, No. 17, 3887-3897.

Dussel, R. et al. (1991 ). "Isocyanide Arene-Ruthenium(ll) Complexes and Activation of Alkenylacetylenes: Synthesis and Characterization of Isocyanide Carbene- and Mixed Carbene-Ruthenium Compounds," Organometallics 10 (9):3287-3291.

Fu et al., "Catalytic Ring-Closing Metathesis of Functionalized Dienes by a Ruthenium Carbene Complex," Journal of the American Chemical Society, Oct. 20, 1993, vol. 115, No. 21, 9856-9857.

Forstner, A. et al. (1998). "Cationic Ruthenium Allenylidene Complexes as a New Class of Performing Catalysts for Ring Closing Metathesis," Chemical Communications (12): 1315-1316.

Furstner, Alois, et al., "Coordinatively unsaturated ruthenium allenylidene complexes: highly effective, well defined catalysts for the ring-closure metathesis of alpha,omega-dienes and dienynes", Chem. Commun., Apr. 7, 1999, pp. 601-602.

Gonzalez et al., "Synthesis of (PCy3)2Cr(C0)3 and Its Reactions With Hydrogen, Nitrogen, and Other Ligands", Journal of the American Chemical Society, 1988, vol. 110, No. 13, 4419-4421.

Harlow, Karsten J., et al., The first co-ordinatively unsaturated Group 8 allenylidene complexes: insights into Grubbs' vs. Dixneuf-Furstner olefin metathesis catalysts, J. Chem. Soc., Dalton Trans., 1999, pp. 285-291.

Herrmann, W.A. et al. (1998). "A Novel Class of Ruthenium Catalysts for Olefin Metathesis," 11th International Symposium on Homogeneous Catalysis; Retrieved from the Internet: URL:http://chsg-jrbl.st-and.ac.uklconferences/ishc/posters/WeskampT.html on Sep. 6, 2002.

Herrmann et al., "N-Heterocyclic Carbenes," Agnew. Chem. Int. Ed. Engl. 1997, 36, No. 19, 2162-2187.

Huang, Jinkun, et al., "Olefin Metathesis-Active Ruthenium Complexes Bearing a Nucleophilic Carbene Ligand", J. Am. Chem. Soc., Mar. 11, 1999, vol. 121, pp. 2674-2678.

Ivin, Kenneth J., "Some recent applications of olefin metathesis in organic synthesis: A review", Journal of Molecular Catalysis A: Chemical. 1998, vol. 133, No. 1-2, pp. 1-16.

International Search Report, Dec. 23, 1999.

Jafarpour, L. et al. (1999). "(p-cymene)RuLCI2 (L=1 ,3-Bis(2,4,6-trimethylphenyl)imidazol-2-ylidene and 1 ,3-Bis(2,6-17 diisopropylpheny)imidazol-2-ylidene) and Related Complexes as Ring Closing Metathesis Catalysts," Organometallics18(18):3760-3763.

Kocher, C. (1997) "Neue Wege zu N-Heterocyclischen Carbenen und deren Metallkomplexen: Anwendungen in der Homogenkatalysy," Dissertation, Technische Universitat Munchen. pp. 30-59 and 124-172.

Kubas, Gregory J., "Molecular Hydrogen Complexes: Coordination of a Sigma Bond to Transition Metals," Accounts of Chemical Research, Mar. 1988, vol. 21. No. 3, 120-128.

Nguyen et al., "Syntheses and Activities of New Single-Component Ruthenium-Based Olefin Metathesis Catalysts," Journal of the American Chemical Society, Oct. 20, 1993, vol. 115, No. 21, 9858-9859.

Nguyen, S. T., et al. (1995). "The Syntheses and Activities of Polystyrene-Supported Olefin Metathesis Catalysts Based on Cl2(PR3)2Ru=CH—CH=CPh2," J. Organometallic Chem. 497(1): 195-200.

Poster Abstract from The Royal Society of Chemistry Dalton Division, 11th International Symposium on Homogeneous Catalysis, no later than Jul. 17, 1998.

Roper, W. R., et al. (1982). Reactions of a (dichlorocarbene)ruthenium Complex, RuCI2(CCI2)(CO)(PPh3)2, Database Accession No. 98:34726 and J. Organometallic Chem. 233(3):C59-C63.

Schattenmann, Wolfgang C., "Neue Katalysatoren fur die Olefin Metathese", Dissertation, Technische Universitat Munchen, Nov. 12, 1997, XP001543131.

Scholl, M., et al. (1999). "Increased Ring Closing Metathesis Activity of Ruthenium-Based Olefin Metathesis Catalysts Coordinated with lmidazolin-2-ylidene Ligands," Tetrahedron Letters 40:2247-2250.

Scholl, M., et al. (1999). "Synthesis and Activity of a New Generation of Ruthenium-Based Olefin Metathesis Catalysts Coordinated with 1,3-Dimesityl-4,5-dihydroimidazol-2-ylidene Ligands," Organic Letters 1(6):953-956.

(56) References Cited

OTHER PUBLICATIONS

Schurer, S.C., et al. (2000). "Synthesis and Application of a Permanently Immobilized Olefin-Metathesis Catalyst," Angewante Chemie International Edition 39(21):3898-3901.

Schwab et al., "Synthesis and Applications of RuCl2(=CHR)(PR3)2: The Influence of the Alkylidene Moiety on Metathesis Activity," Journal of the American Chemical Society, Jan. 10, 1996, vol. 118, No. 1, 100-110.

Ulman et al., "Relative Reaction Rates of Olefin Substrates With Ruthenium(ll) Carbene Metathesis Initiators," Organometallics, Jun. 8, 1998, vol. 17, No. 12, 2484-2489.

U.S. Appl. No. 60/135,493, filed May 24, 1999, Grubbs et al.

U.S. Appl. No. 60/142,853, filed Jul. 7, 1999, Grubbs et al.

Wanzlick, Dr.-lng. H. W., "Aspects of Nucleophilic Carbene Chemistry," Angew. Chem. International Edition, vol. 1 (1962), No. 2, 75-80.

Weskamp et al., "A Novel Class of Ruthenium Catalysts for Olefin Metathesis", Oct. 2, 1998, Angewandte Chemie, vol. 37, No. 18, pp. 2490-2493.

Weskamp, T., et al. (1999). "Highly Active Ruthenium Catalysts for Olefin Metathesis: The Synergy of N-Heterocyclic Carbenes and Coordinatively Labile Ligands," Angew. Chem. Int. Ed. (Communications) 38(16):2416-2419.

Weskamp, Thomas, "N-Heterocyclische Carbene: Eine neue Generation von Rutheniumkatalysatoren fur die Olefin Metathese", Dissertation, Technischen Universitat Munchen, Apr. 14, 1999. (112 pages).

\* cited by examiner

US 8,859,779 B2

CATALYST COMPLEX WITH CARBENE LIGAND

CROSS REFERENCE TO RELATED APPLICATIONS

This application is a continuation of application Ser. No. 13/041,573, filed Mar. 7, 2011, which is continuation of U.S. Pat. No. 7,902,389, issued Mar. 8, 2011, which is a continuation of U.S. Pat. No. 7,622,590, issued Nov. 24, 2009, which claims priority from U.S. Provisional Application Ser. No. 60/099,722, filed Sep. 10, 1998, and Ser. No. 60/115,358, filed Jan. 8, 1999.

STATEMENT AS TO FEDERALLY SPONSORED RESEARCH

This invention was made with Government support under Grant No. CHE-963611 awarded by the National Science Foundation. The Government has certain rights in this invention.

BACKGROUND OF THE INVENTION

The invention relates to metal carbene complexes. More particularly, it relates to catalyst systems comprising metal carbene complexes.

Catalysts previously known in the art are described in, for example, U.S. Pat. No. 5,312,940 to Grubbs et al. These catalysts include bis(phosphine) complexes which involve the use of costly phosphine ($PR_3$) ligands. The stabilities of such systems, as determined by, for example, P—C bond degradation at elevated temperature, are limited. Also, the rates at which bis(phosphine) catalysts carry out particular reactions are limited. Thus, industrial applications involving large-scale syntheses are not as efficient as they could be.

Previously available catalytic systems are also limited in their ability to make highly substituted ring-closing metathesis (RCM) products. Thus, bis(phosphine) catalysts cannot reliably close dienes to make tri-substituted cyclic alkenes, and they fail to make tetra-substituted cyclic alkenes in all but a few cases. Although Schrock catalysts are available to carry out this type of reaction, such systems are quite sensitive.

Thus there exists in the art a need for a generally air- and moisture-sensitive catalyst system able to carry out RCM reactions efficiently and reliably, and also without excessive thermal sensitivity.

SUMMARY OF THE INVENTION

The invention provides catalysts including metal carbene complexes which are useful for synthetic chemical reactions. The catalysts include at least one bulky nucleophilic carbene ligated to the metal center. Methods of making such catalysts, and ligands useful for such catalysts are also provided in the present invention.

The inventive catalytic complexes are thermally stable, have high reaction rates, and are air- and moisture-stable. The catalysts of the invention are easy to synthesize, have high catalytic activity, and are relatively inexpensive, due to the availability of the nucleophilic carbene ligand. The catalysts are useful in the facilitation of chemical reactions, including applications in the pharmaceutical industry, fine chemical synthesis, and the synthesis of polymers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention includes a catalytic complex for the carrying out of chemical reactions. The complex includes a metal atom and various ligands. A particular embodiment of the catalytic complex is depicted in FIGS. 1A, 1B and 1C.

Figure 1A:
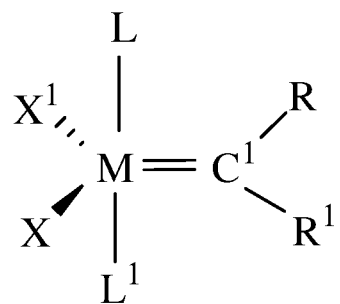
FIG. 1A is a general structure of a first particular embodiment of a catalytic complex, having a first ligation pattern.
Figure 1B:
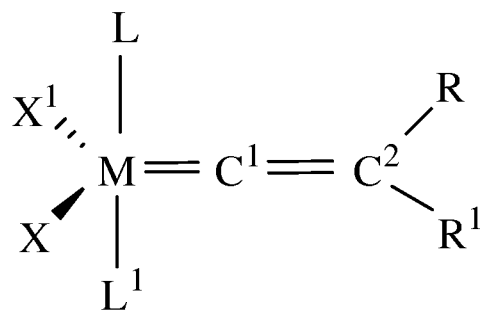
FIG. 1B is a general structure of a first particular embodiment of a catalytic complex, having a second ligation pattern.
Figure 1C:
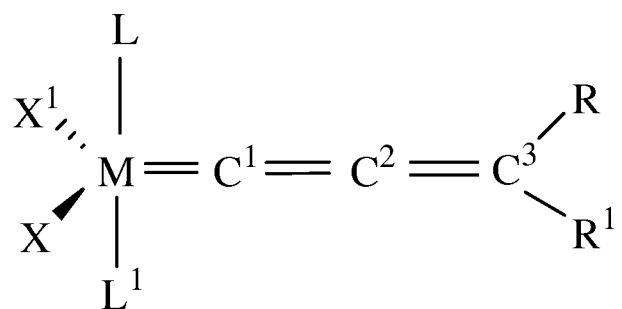
FIG. 1C is a general structure of a first particular embodiment of a catalytic complex, having a third ligation pattern.

Making reference to FIG. 1A, metal atom M can be a transition metal generally having an electron count of from 14 to 18. Particular metals of this description which have been found useful in the present invention include ruthenium and osmium.

Ligated to metal atom M are a number of ligands. At least one of these ligands is a carbene ligand, which is functionally an olefin metathesis active fragment, having a carbon atom $C^1$ which can be further bonded up to two other groups. The bond from metal atom M to carbon atom $C^1$ can be formulated as the double bonded M=$C^1$, although other canonical forms are evidently involved, as detailed in Cotton and Wilkinson's *Advanced Inorganic Chemistry*, 5th Edition, John Wiley & Sons, New York (1980), pp. 1139-1140.

As noted, carbon atom $C^1$ can further bonded to up to two other groups, R and $R^1$, and in this case the olefin metathesis active fragment is referred to as an alkylidene. These R and $R^1$ groups are independently selected from a large number of atoms and substituents. These include hydrogen, alkyl groups having from 1 to 20 carbon atoms (such as methyl, ethyl, n-propyl, iso-propyl, n-butyl, iso-butyl, sec-butyl, and the like). Also possible as either R or $R^1$ are alkenyl or alkynyl substituents having from 2 to 20 carbon atoms. The groups R and $R^1$ can also include alkoxycarbonyl substituents having from 2 to 20 carbons atoms, aryl groups, carboxylate substituents having from 1 to 20 carbon atoms, alkoxy substituents having from 1 to 20 carbon atoms, alkenyloxy or alkynyloxy substituents having from 2 to 20 carbon atoms, as well as aryloxy substituents. Also included are alkylthio, alkylsulfonyl, and alkylsulfinyl substituents with from 1 to 20 carbon atoms. Each of the above classes of R or $R^1$ substituent can be further optionally substituted with halogen, or with alkyl or alkoxy groups of from 1 to 10 carbon atoms, or aryl groups. Further substitution of R and $R^1$ can include the functional groups of hydroxyl, thiol, thioether, ketone, aldehyde, ester, amide, amine, imine, nitro, carboxylic acid, disulfide, carbonate, isocyanate, carbodiimide, carboalkoxy, carbamate, and halogen.

Any of the above R or $R^1$ substituents can include various structural isomers (n-, iso-, sec-, and tert-), cyclic or polycyclic isomers, and multiply unsaturated variants.

Particularly useful R and $R^1$ substituents are vinyl, phenyl, hydrogen, wherein the vinyl and phenyl substituents are optionally substituted with one or more moieties selected from $C_1$-$C_5$ alkyl, $C_1$-$C_5$ alkoxy, phenyl or a functional group, such as chloride, bromide, iodide, fluoride, nitro, or dimethylamine.

When carbon atom $C^1$ is not directly bonded to two groups R and $R^1$, it is further bonded to another carbon $C^2$, which is in turn bonded to previously described substituents R and $R^1$, and the olefin metathesis active carbene ligand is referred to as a vinylidene. This is shown in FIG. 1B. This ligation is generally achieved by means of a double bond from $C^1$ to $C^2$.

Also, as shown in FIG. 1C, $C^2$ can be further bonded to another carbon $C^3$. This type of olefin metathesis active carbene ligand is referred to as an allenylidene. $C^3$ is further bonded to the above-described substituents R and $R^1$. Carbons $C^1$, $C^2$ and $C^3$ are each $sp^2$ hybridized carbons, and the absence of one or two of such carbons in the allenylidene structure of FIG. 1C gives the respective vinylidene or alkylidene or FIG. 1B or 1A, respectively.

It has been found that when R or $R^1$ are aryl, the allenylidene ligand can undergo a rearrangement, forming a different structure in which a ring is formed between $C^1$ and an aryl carbon of R or $R^1$. For example, if $C^1$=$C^2$=$C^3Ph_2$ is ligated to metal M in the systems described herein, the olefin metathesis active carbene ligand is not an allenylidene, but rather a cyclized vinyl carbene, an "indenylidene" (in this case phenylindenylidene).

Also ligated to metal atom M are ligands X and $X^1$ which are anionic ligands, shown in FIGS. 1A, 1B and 1C. Such anionic ligands include those independently chosen from halogen, benzoate, $C_1$-$C_5$ carboxylate, $C_1$-$C_5$ alkoxy, phenoxy, and $C_1$-$C_5$ alkylthio groups. In other particular embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, brosylate, or trifluoromethanesulfonate. In other particular embodiments, both X and $X^1$ are chloride. Ligands X and $X^1$ can further be bonded to each other, forming a bidentate anionic ligand. Examples include diacid salts, such as dicarboxylate salts. As discussed herein, such groups can alternatively be further bound to a solid phase, for example a polymer support.

Also ligated to metal atom M are ligands L and $L^1$. These ligands are chosen from a number of different chemical classes.

One of these classes of ligands L or $L^1$ is the class of nucleophilic carbenes. In the inventive catalytic complexes, at least one of the ligands L or $L^1$ is a member of this class. Nucleophilic carbenes are those molecules having a carbon atom which bears a lone pair of electrons, desirably also including those molecules additionally having electron-withdrawing character manifested in atoms or substituents in electronic communication with, or bonded to, the carbon bearing the lone pair. Such electron withdrawing atoms or substituents can include atoms which are more electronegative than carbon, such as nitrogen, oxygen, and sulfur. These atoms can either be bonded directly to the carbene carbon, or in a conjugated or hyperconjugated position with respect to this carbon. Substituents which have electron-withdrawing character include nitro, halogen, sulfonate, carbonate, sulfide, thioether, cyano, and other groups known to those in the art.

In particular embodiments, it has been found to be desirable that not both of ligands L and $L^1$ be nucleophilic carbenes, although embodiments in which both L and $L^1$ are nucleophilic carbenes are also operative.

Particularly desirable are nucleophilic carbene ligands further substituted with substituents which increase the steric crowding around the carbon bearing the lone pair of electrons. These groups can be bonded directly to the carbene carbon, within a few atoms of the carbene carbon, or remotely from the carbene carbon, as long as the bulky group is able to inhibit the approach of agents which tend to react with, and destroy the carbene, and consequently disable the catalytic complex as a whole. Thus the stability of the nucleophilic carbene ligand, and the catalyst itself are fostered by the presence of bulky groups which are able to shield the nucleophilic carbene from reaction. It should be noted that the olefin metathesis active carbene fragment is sterically protected from bimolecular decomposition by the large steric umbrella provided by the bulky nucleophilic carbene ligand.

Although the invention is not limited by any particular mechanistic theory, it is believed that such a substituent arrangement can provide steric protection from carbene degradation pathways, including thermally induced degradation. The steric bulk of nucleophilic ligands as described herein can lead to more thermally stable catalysts. Such bulky or sterically hindering groups include branched alkyl groups, aryl groups, and aryl groups having branched alkyl substituents, particularly at the ortho positions of the aryl rings. For example, a nucleophilic carbene ligand having bulky alkyl groups such as tert-butyl, iso-propyl or aryl groups with bulky alkyl groups such as 2,4,6-trialkylphenyl or 2,6-dialkylphenyl interacting with the carbene, could be employed in the present invention. The groups L and $L^1$ can also be further bonded to each other, forming a bidentate ligand wherein either one or both of L and $L^1$ are nucleophilic carbene ligands.

Cyclic nucleophilic carbene ligands are also envisioned. These may have heteroatoms either in the ring, or bonded to the ring. Particularly desirable examples of this type of nucleophilic carbene ligand are those ligands having a carbene carbon between heteroatoms. Examples include dinitrogen rings such as imidazole, disulfur rings such as 1,3-dithiolane, and dioxygen rings such as 2H, 4H— 1,3-dioxine. The aromatic, non-aromatic, saturated or unsaturated analogs can be used as well.

Figure 2A:
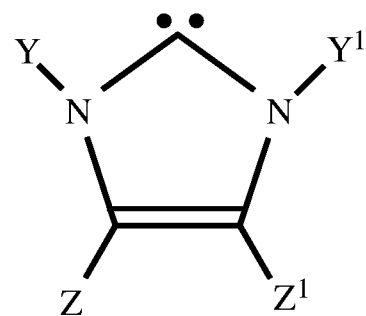
FIG. 2A is an example of a nucleophilic carbene ligand which can be utilized in certain embodiments of the present invention.

FIG. 2A depicts an example of a nucleophilic carbene ligand which can be utilized in certain embodiments of the present invention. Shown is an imidazol-2-ylidene having substituents Y and $Y^1$, and Z and $Z^1$. Each substituent is independently selected from a number of carbon-containing groups, or from hydrogen. The carbon-containing groups which can comprise Y, Y$^1$, Z and Z$^1$ include alkyl groups having from 1 to 20 carbon atoms (such as methyl, ethyl, n-propyl, iso-propyl, n-butyl, iso-butyl, sec-butyl, and the like). Also possible are alkenyl or alkynyl substituents having from 2 to 20 carbon atoms. The groups can also include alkoxycarbonyl substituents having from 2 to 20 carbons atoms, aryl groups, carboxylate substituents having from 1 to 20 carbon atoms, alkoxy substituents having from 1 to 20 carbon atoms, alkenyloxy or alkynyloxy substituents having from 2 to 20 carbon atoms, as well as aryloxy substituents. Each of the above classes of substituent can be further optionally substituted with halogen, or with alkyl or alkoxy groups of from 1 to 5 carbon atoms.

Any of the above substituents can include all structural isomers (n-, iso-, sec-, and tert-), cyclic or polycyclic isomers, and multiply unsaturated variants. It should also be noted that the presence of the double bond in the imidazole ring is not required for catalytic activity in the present invention. In certain embodiments, an imidazolidin-2-ylidene can be used as nucleophilic carbene ligand L or L$^1$.

Figure 2B:
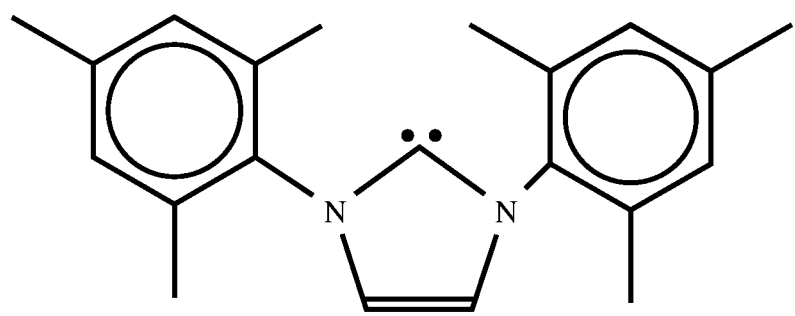
FIG. 2B is a particular nucleophilic carbene which can be utilized in certain embodiments of the invention.
Figure 2C:
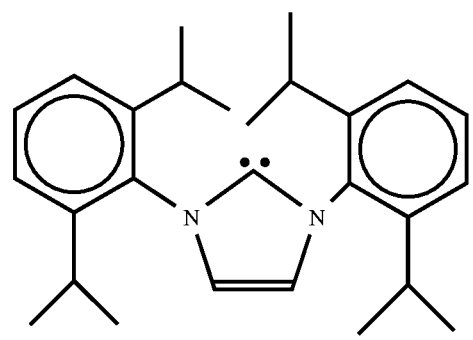
FIG. 2C is a particular nucleophilic carbene which can be utilized in certain embodiments of the invention.

The structure in FIG. 2B is a particular example of a useful nucleophilic carbene ligand, having both Y and Y$^1$ as 2,4,6-trimethylphenyl, and both Z and Z$^1$ as hydrogen. This particular ligand is referred to as 1,3-bis(2,4,6-trimethylphenyl)imidazol-2-ylidene, or IMes. Another example of a useful nucleophilic carbene is given in FIG. 2C, which shows a structure having both Y and Y$^1$ as 2,6-diisopropylphenyl, and both Z and Z$^1$ as hydrogen. This particular ligand is referred to as 1,3-bis(2,6-diisopropylphenyl)imidazol-2-ylidene, or IPr.

Another class of ligand which can serve as L or L$^1$ is the class of phosphines. Particularly useful are trialkyl- or triarylphosphines, such as trimethylphosphine, triphenylphosphine, triisopropylphosphine, and similar phosphines. The phosphines tricyclohexylphosphine and tricyclopentylphosphine are also useful, and are collectively referred to as PCy$_3$.

Other classes of ligands which can serve as L or L$^1$ are sulfonated phosphines, phosphites, phosphinites, phosphonites, arsine, stibine, lmmes, ethers, amines, amides, sulfoxides, carbonyls, carboxyls, nitrosyls, pyridines, and thioethers.

Figure 3A:
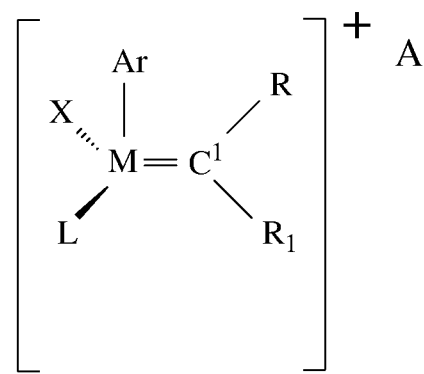
FIG. 3A is a general structure of a second particular embodiment of a catalytic complex, having a first ligation pattern.
Figure 3B:
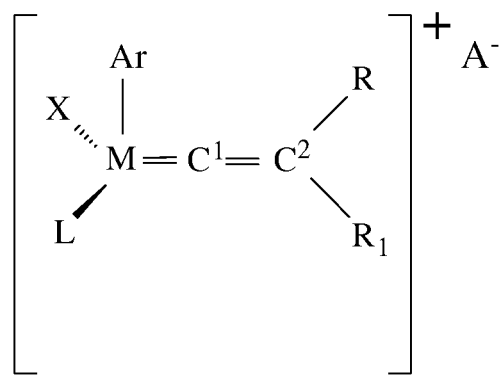
FIG. 3B is a general structure of a second particular embodiment of a catalytic complex, having a second ligation pattern.
Figure 3C:
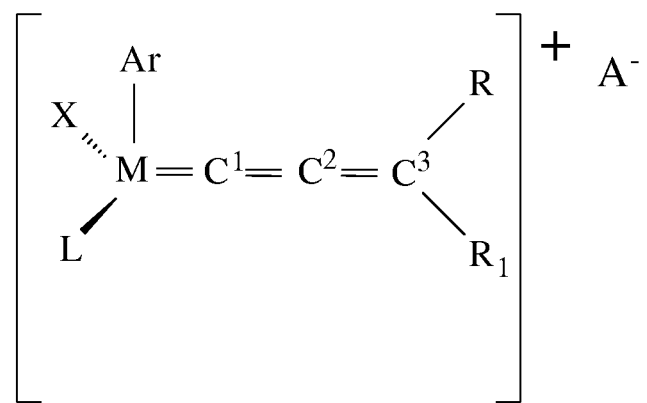
FIG. 3C is a general structure of a second particular embodiment of a catalytic complex, having a third ligation pattern.

Other embodiments of catalytic complexes useful in the present invention are shown in FIGS. 3A (alkylidene), 3B (vinylidene) and 3C (allenylidene), in which the analogy with the series of FIGS. 1A, 1B and 1C is based on the identity of the olefin metathesis active carbene ligand, alkylidene, vinylidene and allenylidene, respectively. The elements M, X, C$^1$, C$^2$, C$^3$, R and R$^1$ are as described above for the first described embodiment of the inventive catalytic complex. In this second particular embodiment, ligand L is a nucleophilic carbene ligand, as described above. In addition, since the species depicted in FIGS. 3A, 3B, and 3C are all cationic complexes, an anion A$^-$ is required. This anion can be any inorganic anion, and can also include some organic anions. Thus, A$^-$ can be, for example, halide ion, SbF$_6^-$, PF$_6^-$, BF$_4^-$—, AsCl$_4^-$—, O$_3$SONO$^-$, SO$^2$F$^-$, NSO$_3^-$, azide, nitrite, nitrate, or acetate, and many others known to those of skill in the art.

In this embodiment, another ligand of metal M is Ar, which is an aromatic ring system, including the η$^6$-bonded system. The symbol η is used to signify that all aromatic ring atoms are bonded to the metal atom. Such systems include C$_6$H$_6$ ring systems, and various alkyl substituted C$_6$H$_6$ ring systems. Heterocyclic arene rings are also suitable, and these include η$^6$—C$_5$H$_5$N, and alkyl substituted derivatives thereof. These rings can have substituents chosen from a wide range of groups including alkyl groups having from 1 to 20 carbon atoms (such as methyl, ethyl, n-propyl, iso-propyl, n-butyl, iso-butyl, sec-butyl, and the like). Also possible are alkenyl or alkynyl substituents having from 2 to 20 carbon atoms. The groups can also include alkoxycarbonyl substituents having from 2 to 20 carbons atoms, aryl groups, carboxylate substituents having from 1 to 20 carbon atoms, alkoxy substituents having from 1 to 20 carbon atoms, alkenyloxy or alkynyloxy substituents having from 2 to 20 carbon atoms, as well as aryloxy substituents. Each of the above classes of substituent can be further optionally substituted with halogen, or with alkyl or alkoxy groups of from 1 to 5 carbon atoms. For example, useful η$^6$-bonded L or L$^1$ ligands are p-cymene, fluorene and indene.

The inventive catalytic complexes can be used as homogeneous catalysts, or are equally well suited as heterogeneous catalysts. The latter embodiment is realized by linking the catalytic complexes to a suitable solid phase, such as a polymeric support. The solid phase can be bound to the catalytic complex either cleavably or non-cleavably. The solid phase can be a polymer which can either be a solid-state resin such as a Wang resin, or a soluble polymer such as non-crosslinked chloromethylated polystyrene (NCPS). This polymer shows excellent properties, such as solubility in tetrahydrofuran (THF), dichloromethane, chloroform, and ethyl acetate, even at low temperatures (−78° C). NCPS is insoluble in water and methanol. These features allow traditional organic chemistry techniques such as solvent extraction, and methanol precipitation. Suitable polymers include hydroxyl-containing polymers such as Wang resin, or poly(ethylene glycol) (PEG).

The method of attachment between solid phase and catalytic complex can take the form of a link to the ligand L or L$^1$, which is desirably the nucleophilic carbene ligand. This arrangement is desirable since the catalytic complex is believed to operate by first releasing the ligand which is not a nucleophilic carbene, for example, by releasing a phosphine ligand. Thus, linkage to the phosphine ligand would result in loss of the solid phase-catalytic complex interaction, upon catalysis. Also considered desirable is linkage of the catalytic complex to a solid phase through the anionic ligands X and/or X$^1$. Thus, any linkage which involves a group serving as an anionic ligand as described above can be used to attach the catalytic complex to a solid support. For example, carboxylate resins can be employed for this purpose.

The inventive catalytic complexes are air- and moisture-stable, and thus can be used under atmospheric conditions, and even in aqueous environments. The stability of the catalytic substrates and products will be the limiting factors with respect to use under such conditions. The inventive catalytic complexes are soluble in typical organic solvents, such as tetrahydrofuran (THF), benzene, toluene, xylene, diethyl ether, dioxane, alcohols, acetonitrile, dimethylsulfoxide (DMSO), dimethylformamide (DMF), and similar solvents, but not particularly soluble in water or methanol.

The catalytic complexes need not be used in the presence of any initiators or cocatalysts, although materials such as phosphine sponges can optionally be used. Those of skill in the art will recognize the identity of the members of this class, which includes copper chloride, and Lewis acids generally, in concentrations up to those stoichiometric with that of the catalytic complex.

Use of Catalytic Complexes in Ring-Closing Metathesis (RCM)

The catalytic complexes can be used for ring-closing metathesis. This reaction converts a diterminal diene (a compound having two —$C^a$=$C^bH_2$ groups, the $C^a$ atoms of which are able to link together to form a cyclic compound with a —$C^a$=$C^a$— linkage), to a cyclic alkene, with $H_2C^b$=$C^bH_2$ as a side product. In some instances, the diterminal diene (or an α, ω diene) can undergo a 1,3-hydrogen shift rearrangement (to give an α, ω−1 diene), and the product will be a cyclic alkene with one less methylene group in the ring, and propene as a side product.

A pronounced solvent dependence of the reactivity of the present catalytic complexes was noticed. As can be seen from the results compiled in Scheme 1, reaction rates for (IMes)(PCy$_3$)Cl$_2$Ru(=CHPh) in toluene are substantially higher than those in CH$_2$Cl$_2$ (the substituent E is —CO$_2$Et). Thus, the tetrasubstituted cyclohexene derivative of Scheme 1 is formed in essentially quantitative yield after only 15 min if the reaction is carried out in toluene. The reaction requires 2-3 hours in CH$_2$Cl$_2$ to reach completion. This influence of the reaction medium has been observed for the ruthenium carbene complexes bearing N-mesityl substituents on their imidazol-2-ylidene ligands. However, the related complexes having N-cyclohexyl or N-isopropyl groups do not show this effect.

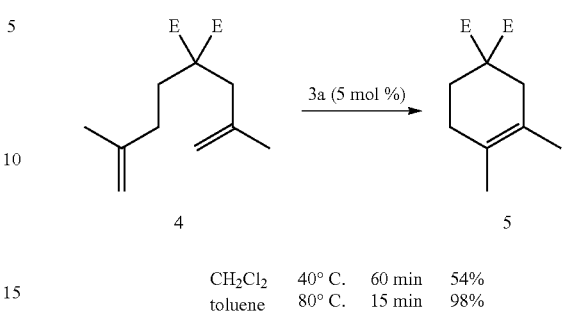

Scheme 1. Solvent Dependence of the Reactivity of Complex (IMes)(PCy$_3$)Cl$_2$Ru(=CHPh)

| | | | |
|---|---|---|---|
| CH$_2$Cl$_2$ | 40° C. | 60 min | 54% |
| toluene | 80° C. | 15 min | 98% |

This reactivity of (IMes)(PCy$_3$)Cl$_2$Ru(=CHPh) in toluene is impaired by a tendency of the active species to promote isomerization of the double bonds of the substrate. Thus, in Scheme 2, treatment of the pictured diene with as little as 1.2 mol % of (IMes)(PCy$_3$)Cl$_2$Ru(=CHPh) in toluene leads to complete consumption of the starting material within 45 min, but delivers significant amounts of the 20-membered ring in addition to the desired 21-membered lactone. Although not wishing to be bound by any particular theory, the cis-cyclic alkene is believed to result from an initial isomerization of one of the double bonds in the starting material, followed by elimination of propene instead of ethylene during ring closure. This intrinsic bias for ring contraction was not suppressed by lowering the reaction temperature. In stark contrast, however, only minute amounts of the cis-alkene are detected if the reaction is performed in CH$_2$Cl$_2$.

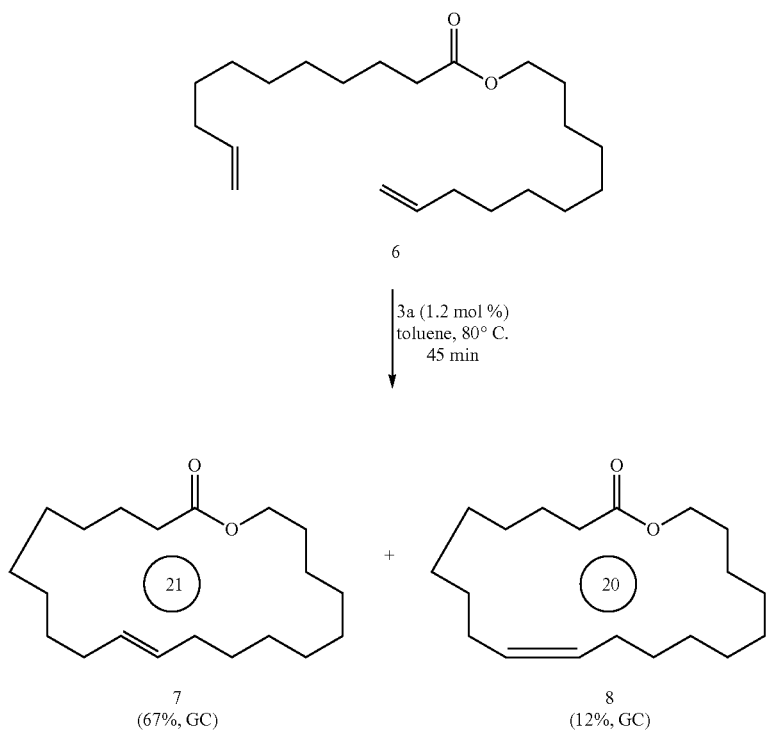

Scheme 2. Stereochemistry

As can be seen from the results compiled in Table 1, the reactivities of (IMes)(PCy$_3$)Cl$_2$Ru(=CHPh) and (IMes)(PCy$_3$)Cl$_2$Ru(phenylindenylidene) in CH$_2$Cl$_2$ are sufficiently high to allow the preparation of di-, tri- and even tetrasubstituted cyclo-alkenes in good to excellent yields. All ring sizes including medium and macrocyclic ones can be accessed. The yield data given are the isolated yields. The reactions with yields given with superscript b (entries 1-4) were carried out in toluene at 80° C. The compound 3a refers to (IMes)(PCy$_3$)Cl$_2$Ru(=CHPh), and 3b to (IMes)(PCy$_3$)Cl$_2$Ru(phenylindenylidene). E is —CO$_2$Et.

TABLE 1

RCM catalyzed by (IMes)(PCy$_3$)Cl$_2$Ru(=CHPh) and (IMes)(PCy$_3$)Cl$_2$Ru(phenylindenylidene) in CH$_2$Cl$_2$

| Entry | Product | Catalyst (mol %) | Yield (%) |
|---|---|---|---|
| 1 | 3,4-dimethyl-1-(SO$_2$Ph)-2,5-dihydropyrrole | 3a (2%) | 96[b] |
| 2 | (same as entry 1) | 3b (2%) | 97[b] |
| 3 | 3,3-bis(CO$_2$Et)-1,2,4-trimethylcyclopent-1-ene (E = CO$_2$Et) | 3a (5%) | 77[b] |
| 4 | bis(E)-substituted tetramethylcyclohexene | 3b (2%) | 89[b] |
| 5 | E-substituted bicyclic (hydrindane-type) | 3a (5%) | 98 |
| 6 | E-substituted bicyclic | 3a (5%) | 93 |
| 7 | bis(E)-substituted dimethylcycloheptene | 3b (5%) | 71 |
| 8 | N-Ts azocene | 3a (1%) | 64 |
| 9 | bicyclic oxazolidinone-fused cyclooctene (R = H) | 3a (1%) | 62 (R = H) |
| 10 | (R = Me) | 3a (5%) | 95 (R = Me) |
| 11 | pentadec-10-enolide (macrolactone) | 3a (2%) | 72 |
| 12 | macrolactam | 3a (3%) | 82 |
| 13 | macrolactone | 3a (4%) | 71 |

It must be noted that most of these cyclizations cannot be carried out if the bis(phosphine) complex (PCy$_3$)$_2$Cl$_2$Ru(=CHPh) is used as the catalyst. This holds true for all tetrasubstituted cases (entries 1-4 and 7), the trisubstituted 8-membered ring shown in entry 10, as well as for annulation reactions depicted in entries 5 and 6. Although the macrocyclic products (entries 11-13) can also be obtained with the use of (PCy$_3$)$_2$Cl$_2$Ru(=CHPh), using (IMes)(PCy$_3$)Cl$_2$Ru(=CHPh) results in shorter reaction times and allows lower catalyst loadings to be employed. This aspect is particularly relevant with respect to pentadec-10-enolide (entry 11) which is converted into the valuable, musk-odored perfume ingredient EXALTOLIDE® (=pentadecanolide) upon simple hydrogenation.

As can be deduced from the results in Table 1, complex (IMes)(PCy$_3$)Cl$_2$Ru(=CHPh) bearing a benzylidene carbene moiety and complex (IMes)(PCy$_3$)Cl$_2$Ru(phenylindenylidene) with a phenylindenylidene unit are essentially equipotent pre-catalysts.

Method of Making Catalytic Complexes

The inventive catalytic complexes can be made according to the following general synthetic procedures, which are adapted from known procedures.

To synthesize a catalytic complex according to a first embodiment of the invention, one of the two phosphine ligands of a diphosphine-ligated ruthenium or osmium catalyst is exchanged with a nucleophilic carbene ligand. For example, starting material diphosphine-ligated complexes (PCy$_3$)Cl$_2$Ru(=CHPh) and (PPh$_3$)Cl$_2$Ru(=CHPh) can be synthesized according to general procedures such as those given by Schwab et al., *Angew. Chem. Intl. Ed. Engl.*, (1995) 34, 2039-41.

Ligand-exchange reactions are carried out by exposing the diphosphine-ligated complexes to nucleophilic carbene ligands, as defined above, in suitable solvents such as THF, toluene, and the like. Reactions are generally carried out at temperatures of from about 0° C. to about 50° C., for about 15 minutes to several hours. Subsequent recrystallization in inert solvents gives the complexes in good yield and high purity.

The nucleophilic carbene ligands according to the invention are synthesized according to the following general synthetic procedure. Solutions of heteroatom-containing starting material such as aniline, or substituted aniline, phenol or substituted phenol, benzenethiol or substituted benezenethiol, primary- or secondary-amines, alcohols and thiols can be prepared in solvents such as tetrahydrofuran (THF), benzene, toluene, xylene, diethyl ether, dioxane, alcohols, acetonitrile, dimethylsulfoxide (DMSO), dimethylformamide (DMF), water, and similar solvents, under an inert atmosphere. Substituents for the above groups include alkyl groups having from 1 to 20 carbon atoms (such as methyl, ethyl, n-propyl, iso-propyl, n-butyl, iso-butyl, sec-butyl, and the like). Also possible are alkenyl or alkynyl substituents having from 2 to 20 carbon atoms. The groups can also include alkoxycarbonyl substituents having from 2 to 20 carbons atoms, aryl groups, carboxylate substituents having from 1 to 20 carbon atoms, alkoxy substituents having from 1 to 20 carbon atoms, alkenyloxy or alkynyloxy substituents having from 2 to 20 carbon atoms, as well as aryloxy substituents. Each of the above classes of substituent can be further optionally substituted with halogen, or with alkyl or alkoxy groups of from 1 to 5 carbon atoms. Particularly useful are those substituents such as methyl, ethyl, propyl, and butyl, including branched isomers, and aryl substituents at the ortho- or diortho-positions (for example, 2- or 2,6-substitution for benzyl rings).

The solution is then contacted with an approximately one half of equimolar amount (with respect to the heteroatom-containing starting material) of paraformaldehyde. After heating to dissolve paraformaldehyde, the contents of the flask are acidified with an approximately one half of equimolar amount (with respect to the heteroatom-containing starting material) of mineral acid (for example, hydrochloric acid or nitric acid).

At this stage, if a nitrogen-containing starting material (aniline-derivative or primary amine-derivative) is used, an approximately one half of equimolar amount (with respect to the heteroatoms-containing starting material) of a dialkoxyacetaldehyde is added drop wise after a few minutes of stirring. The dialkoxyacetaldehyde can be dimethoxy-, diethoxy-, dipropoxy-, dibutoxy-, diphenoxy, or can be any of a number of combinations of such alkoxy substituents such as for example methoxyethoxy, or methoxyphenoxy. The procedure then continues as follows.

If, on the other hand, oxygen or sulfur heteroatom-containing starting material is used, the above paragraph is not followed, and the procedures from this point on are common to all starting materials. After equipping the reaction flask with a Dean-Stark trap, or similar device, the mixture is heated to a temperature of from about 80° C. to about 180° C., preferably from about 100° C. to about 150° C. for several hours (from about 5 to about 30 hours). During this time, a precipitate forms, as the side products of water and methanol, as well as some solvent, are removed. The reaction mixture is stirred at room temperature for a time ranging from about 20 minutes to about 4 hours, preferably from 1 to 3 hours. Precipitate will have formed during this time.

The precipitate is filtered, washed with a suitable solvent, such as THF to give the nucleophilic carbene product in the form of a salt. For example, if aniline or substituted aniline is used, the product will be a 1,3-diarylimidazole salt. If the starting material is a primary amine, the product will be a 1,3-dialkyl imidazole salt. Either of these products can be converted to the saturated heterocyclic derivative (imidazolidine) by conventional hydrogenation techniques such as exposure to H$_2$ over a carbon-palladium or carbon-platinum catalyst. Such techniques will be recognized and known to those of skill in the art. If the starting material is a phenol- or thiobenzene-derived compound, the product will be a dibenzoxymethane-, or dibenzthiomethane-product. If the starting material is an alcohol or thiol, the product will be a 1,1-bis(alkoxy)methane- or 1,1-bis(alkylthio)methane-product.

The second embodiments of the catalytic complexes of the invention are easily made by combining a precursor species of the catalytic complexes with an acetylene to give the allenylidene type of catalytic complex (see FIG. 3C). An example of this precursor species of the catalytic complex is shown below.

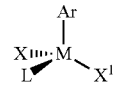

In this structure, metal M, and ligands X, X$^1$, L and Ar are defined as above, with L being a nucleophilic carbene. This precursor species is generally available in the form of a dimer [ArRuCl$_2$]$_2$, which is converted to the precursor species when the dimer is exposed to a nucleophilic carbene in a suitable solvent such as THF, hexanes and other non-protic solvents. For example, the dimer [(p-cymene)-RuCl$_2$]$_2$ is commercially available from Strem Chemicals (Newburyport, Mass.).

The acetylenes with which precursor species of the inventive catalytic complexes combine to form second embodiments of the invention are terminal acetylenes, and can be substituted at the y-position with alkyl or aryl groups, or optionally further substituted with halogen, or with alkyl or alkoxy groups of from 1 to 10 carbon atoms, or aryl groups. Further substitution can include the functional groups of hydroxyl, thiol, thioether, ketone, aldehyde, ester, amide, amine, imine, nitro, carboxylic acid, disulfide, carbonate, isocyanate, carbodiimide, carboalkoxy, carbamate, and halogen. Particularly useful substituents are vinyl, phenyl, or hydrogen, wherein the vinyl and phenyl substituents are optionally substituted with one or more moieties selected from C$_1$-C$_5$ alkyl, C$_1$-C$_5$ alkoxy, phenyl or a functional group, such as chloride, bromide, iodide, fluoride, nitro, or dimethylamine.

The invention will be further described in the following examples, which do not limit the scope of the invention described in the claims.

EXAMPLES

Illustrations of methods of making certain embodiments of the inventive catalytic complexes, as well as properties thereof, are provided by the following examples.

Example 1

Synthesis of IMes-HCl

A 300 mL Schlenk flask was charged with 2,4,6-trimethylaniline (10 g, 74 mmol), toluene (50 mL), and paraformaldehyde (1.11 g, 37 mmol) under argon and heated to 110° C. until all the paraformaldehyde was dissolved. The flask was then cooled to 40° C. and HCl (6.17 mL, 6N, 37 mmol) was added to the reaction mixture drop wise. The mixture was stirred at that temperature for 10 minutes before dimethoxyacetaldehyde (6.442 g, 60% wt. in water, 37 mmol) was added in drop wise fashion. The flask was then equipped with a Dean-Stark trap and heated to 120° C. for 15 hours, during which time a dark precipitate was formed and grew in volume by removal of the side-products ($H_2O$ and methanol) and some of the solvent through the Dean-Stark trap. The reaction mixture was then allowed to cool to room temperature and stirred at that temperature for two hours. Filtration of the precipitate through a Schlenk frit, washing with tetrahydrofuran (three times, 20 mL each wash), and drying yielded a white solid in 60% yield, which was characterized spectroscopically as pure IMes-HCl. $^1$H NMR: δ=2.12 (s, 12H, o-$CH_3$), 2.30 (s, 6H, p-$CH_3$), 6.97 (s, 4H, mesityl), 7.67 (s, 2H, NCHCHN), 10.68 (s, 1H, HCl).

Example 2

Synthesis of iMes

In a glovebox, a 300 mL Schlenk flask equipped with a stir bar was charged with 20.0 g (58.7 mmol) of IMes-HCl and 120 mL of dry tetrahydrofuran. The resulting suspension was stirred for 10 minutes after which time 6.80 g (60.7 mmol) of solid potassium tert-butoxide was added to the suspension at room temperature in a single portion. A dark gray solution was obtained immediately. The flask was taken out of the glovebox and connected to the Schlenk line. The solution was stirred for 20 minutes before all volatiles were removed under vacuum. The residue was extracted into warm toluene (120 mL+60 mL+20 mL) and filtered through a medium porosity frit (filtration was rather slow), and the solvent was removed under vacuum to obtain crystals of IMes. The resulting product was recovered in 90% yield, and had a dark tint but was sufficiently pure for its use in further synthesis. Further purification could be achieved by recrystallization from toluene or hexane, yielding colorless crystals.

The synthesis of related carbenes 1,3-bis(4-methylphenyl)imidazol-2-ylidene (ITol) and 1,3-bis(4-chlorophenyl)imidazol-2-ylidene (IpCl) was carried in an analogous fashion.

Example 3

Synthesis of (IMes)(PCy$_3$)(Cl)$_2$Ru(=CHCH=CMe$_2$)

The procedure was carried out under purified and dried argon atmosphere and with dried and degassed solvents. IMes (2.1990 g, 7.221 mmol) was suspended in 250 mL hexanes, into which (Cl)$_2$(PCy$_3$)$_2$Ru(=CHCH=CMe$_2$) (5.0718 g, 7.092 mmol) was added in one portion. The mixture was heated for 2.5 hours with stirring at 60° C. During this period, the formation of an orange-brown precipitate was observed. The volume of the suspension was then reduced in vacuum to 50 mL and the suspension was cooled to −78° C. Following filtration and cold pentane washing of the residue (2 washes, each 20 mL), the product was isolated as a brown orange microcrystalline material in 72% yield (3.97 g).

Example 4

Synthesis of (IMes)(PC)13)CbRu(=CHPh)

The procedure of Example 3 was followed, except that (Cl)$_2$(PCy$_3$)$_2$Ru(=CHPh) was used. This complex was soluble in a variety of organic solvents including hydrocarbon, tetrahydrofuran, acetone, methylene chloride, and diethylether. The identity of the complex was confirmed by X-ray crystallography. Other embodiments will be readily synthesized by substituting the IMes ligand with other nucleophilic carbene ligands.

Example 5

Thermodynamic Studies

The thermodynamics of the following reaction in tetrahydrofuran (THF) at room temperature were studied.

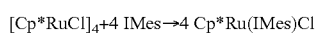

(Cp* is $\eta^5$—$C_5Me_5$) The reaction proceeds rapidly as indicated by the rapid development of a deep blue color in the reaction solution. A deep blue crystalline solid was isolated in 86% yield. Nuclear magnetic resonance data of the blue solid indicated the isolation of a single species bearing a unique Cp* and a single carbene ligand. X-ray crystallography confirmed the formulation of Cp*Ru(IMes)Cl. An enthalpy of reaction of −62.6±0.2 kcal/mol was measured by anaerobic solution calorimetry in THF at 30° C. when 4 equivalents of carbene were reacted with 1 equivalent of the tetramer, [Cp*RuCl]$_4$. Table 2 compares the enthalpy of similar reactions where IMes is replaced with other moieties.

TABLE 2

Comparison of Reaction Enthalpies

| Identity of L in Cp*Ru(L)(Cl) | ΔH (kcal/mol) of reaction: [Cp*RuCl]$_4$ + 4L → 4Cp*Ru(L)(Cl) | Relative stability of Ru-L bond (kcal/mol) |
|---|---|---|
| IMes | −62.6 ± 0.2 | −15.6 |
| P(isopropyl)$_3$ | −37.4 ± 0.3 | −9.4 |
| P(cyclohexyl)$_3$ | −41.9 ± 0.2 | −10.5 |

The IMes ligand proves to be a stronger binder to the Cp*RuCl fragment than PCy$_3$, by 5 kcal/mol. The carbene ligand is a fairly good binder but can be displaced if a better donor ligand, such as a phosphite, is used. The phosphite reaction allows for the construction of a thermochemical cycle which confirms the internal consistency of the calorimetric data, as shown in Scheme 3.

Scheme 3. Thermodynamic Cycle

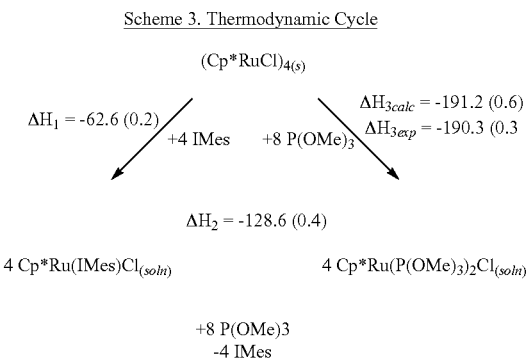

A further verification of the thermochemical results can be made by examining the following hypothetical reaction.

This reaction is calculated to be exothermic by 5 kcal/mol and no entropic barrier is apparent, so the reaction should proceed readily as written. Indeed, upon mixing of the reagents in THF-d$_8$, the characteristic $^{31}$P signal of Cp*Ru(PCy$_3$)Cl disappears (at 11.3 ppm), and that of free PCy$_3$ appears (40.4 ppm), as observed by Campion et al., *J. Chem. Soc. Chem. Commun.*, (1988) 278-280.

Example 6

Structural Studies

Figure 4:
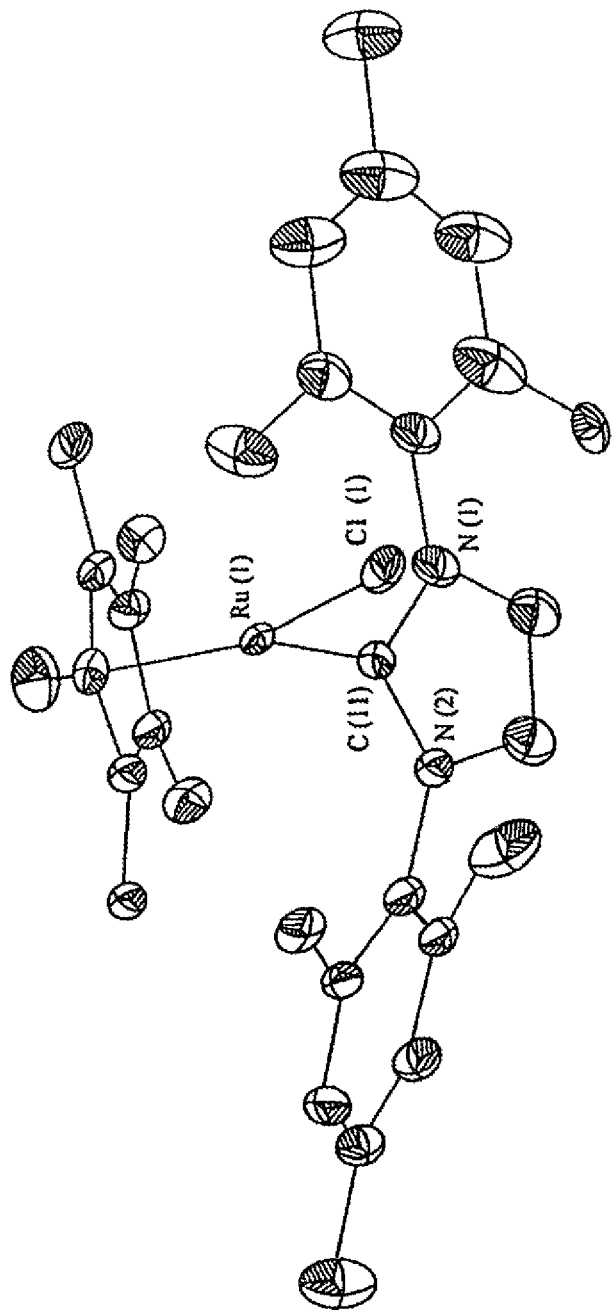
FIG. 4 is an ORTEP diagram of the crystal structure of Cp*Ru(IMes)Cl.
Figure 5:
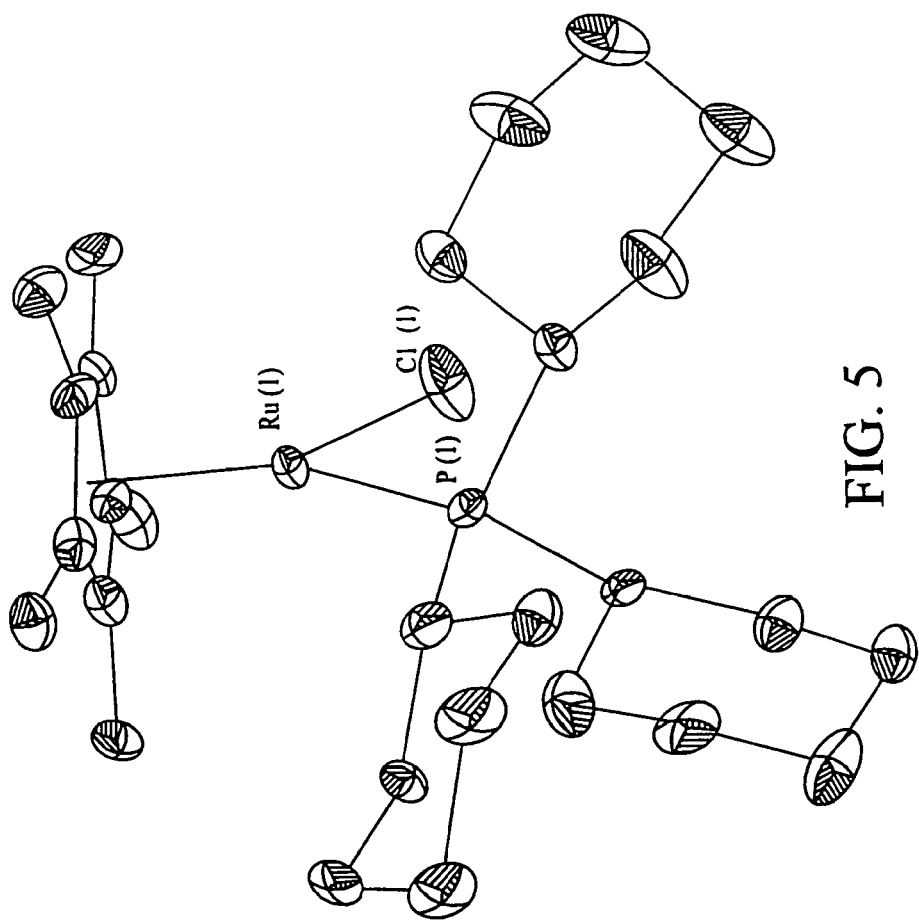
FIG. 5 is an ORTEP diagram of the crystal structure of Cp*Ru($PCy_3$)Cl.
Figure 6:
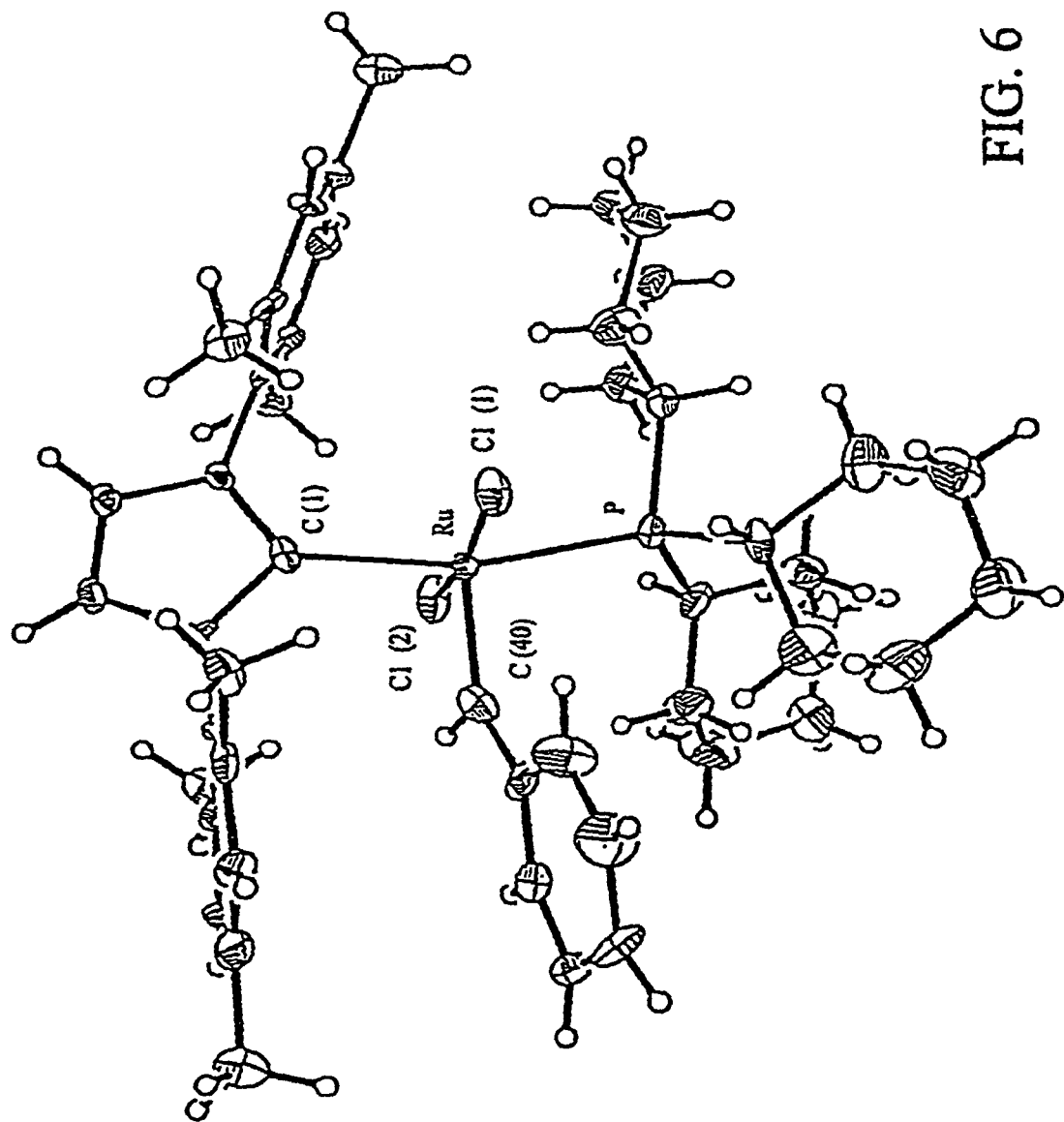
FIG. 6 is an ORTEP diagram of the crystal structure of $Cl_2$Ru($PCy_3$)(IMes) (=CHPh).

In order to gauge the steric factor inherent in the catalytic systems, structural studies were carried out on CP*Ru(IMes)Cl (FIG. 4), Cp*Ru(PCy$_3$)Cl (FIG. 5), and (IMes)(PCy$_3$)Cl$_2$Ru(=CHPh) (FIG. 6). Comparison was made to another sterically demanding ligand in the complex Cp*Ru(P$^i$Pr$_3$)Cl. The following crystal data was obtained. For Cp*Ru(IMes)Cl: monoclinic, space group P2$_{1/c}$, dark blue prism, 0.35× 0.25×0.20, a=10.6715 (2), b=14.3501 (3), c=19.2313 (4), β-103.2670 (10) deg, Z=4, R$_f$=0.0294, GOF=0.888. For Cp*Ru(PCy$_3$)Cl: orthorhombic, space group Pcba, dark blue prism, 0.45×0.35×0.25, a=18.9915 (6), b=15.6835 (5), c=19.0354 (6), Z=8, R$_f$=0.0392, GOF=1.132. For (IMes)(PCy$_3$) ChRu(=CHPh): space group P2$_1$2$_1$2$_1$, yellow-orange prism, a=12.718 (1), b=14.549 (1), c=26.392 (2), R$_f$=0.0616, z=4, GOF=1.038. The metrical data of Cp*Ru(P$^i$Pr$_3$)Cl (Campion et al., *J Chem. Soc. Chem. Commun.*, (1988) 278-280) can be used for comparison: Ru—P, 2.383 (1) Å; Ru—Cl, 2.378 (1) Å; Ru—Cp*(c), 1.771 (1) Å; Cl—Ru—P, 91.2 (1)°:Cl—Ru—Cp*(c), 129.9 (1)°; C(1)-Ru—Cp*(c), 139.9 (1)°.

The three Cp*RuCl(L) structures are similar, with the variation in Ru-L distances the only standout feature, but this is explainable by the difference in covalent radii between P and C. Only slight angle distortions are observed in Cp*Ru(IMes)Cl, presumably to accommodate the bulkiness of IMes. The IMes ligand displays non-coplanar rings with torsion angles of 78.46 (4)° between the arene ring bound to N(2) and the imidazole ring and 78.78 (5)° between the imidazole ring and the arene ring bound to N(1). The two arene rings adopt a mutually staggered configuration.

A direct comparison of the steric properties displayed by IMes and PCy$_3$ provides insight into the significant steric congestion provided by the IMes ligation. The cone angle reported for P$^i$Pr$_3$ and PCy$_3$ are 160° and 170°, respectively (Tolman, *Chem. Rev.* (1977) 77, 313-348). Such a cone angle measurement is not straightforward in the present system. Instead, the crystallographic data can be used to determine closest contact angles involving non-hydrogen atoms in Cp*Ru(IMes)Cl and Cp*Ru(PCy$_3$)Cl. For the Ru—PCy$_3$ fragment, an angle of 96.3° is measured using cyclohexyl methylene carbons on adjacent cyclohexyl rings defining the largest angle. For the Ru—P$^i$Pr$_3$ fragment in Cp*Ru(P$^i$Pr$_3$)Cl a similar angle of 95.8° is obtained. As for the IMes fragment, two parameters can be obtained. Angles of 150.7° and 115.3° are measured for the <4-Me—Ru-4'-Me and <6-Me—Ru-2'-Me angles, respectively. The steric coverage of the IMes ligand can be considered as a fence rather than a cone. The increased steric congestion provided by the IMes ligand compared to PCy$_3$ derives from the presence of bulky substituents on the imidazole nitrogens and, to a greater extent, from the significantly shorter metal-carbon bond distance which brings the entire IMes ligand closer to the metal center.

The structural analysis of (IMes)(PCy$_3$)Cl$_2$Ru(=CHPh) shown in FIG. 6 reveals a distorted square pyramidal coordination with a nearly linear Cl(1)-Ru—Cl(2) angle)(168.62°. The carbene unit is perpendicular to the C(1)-Ru—P plane, and the carbene aryl moiety is only slightly twisted out of the Cl(1)-Ru—Cl(2)-C(40) plane. The Ru—C(40) bond distance (1.841 (11) A) is the same as that in RuCl$_2$(=CH-p-C$_6$H$_4$Cl)(PCy$_3$)$_2$ (1.838 (3) Å) and shorter than that in (PCy$_3$)$_2$RuCl$_2$(=CHCH=CPh$_2$) (1.851 (21)A). While two (formally) carbene fragments are present in (IMes)(PCy$_3$)Cl$_2$Ru(=CHPh), they display different Ru—C distances (Ru—C(40)=1.841 (11) and Ru—C(1)=2.069 (11)Å). These important metrical parameters clearly distinguish two metal-carbene interactions: a metal benzylidene fragment with a formal metal to carbon double bond and a metal imidazolium carbene with a formal metal-carbon single bond. From FIG. 6, it is also clear that the IMes ligand is sterically more demanding than PCy$_3$.

Example 7

Thermal Stability Studies

In the course of catalytic testing, the remarkable air stability of the inventive catalytic complexes was observed. To gauge the robust nature of these carbene complexes in solution, their thermal stability under inert atmosphere was tested at 60° C. The relative order of stability found was (IMes)(PCy$_3$)Cl$_2$Ru(=CHPh)>>(IMes)(PPh$_3$)Cl$_2$Ru(=CHPh)> (PCy$_3$)$_2$Cl$_2$Ru(=CHPh). After 14 days of continuous heating of toluene solutions of (IMes)(PCy$_3$)Cl$_2$Ru(=CHPh) to 60° C., no decomposition was detected (as monitored by both $^1$H and $^{31}$P NMR). In contrast, solutions of (PCy$_3$)$_2$Cl$_2$Ru(=CHPh) showed signs of decompositions after one hour, under the same conditions.

The catalyst (IMes)(PCy$_3$)Cl$_2$Ru(=CHPh) was stable at 100° C. for 36 hours before showing any indication of decomposition. Similar thermal decomposition studies have been conducted in refluxing methylene chloride, dichloromethane, toluene, benzene and diglyme with similar results.

Except as may be expressly otherwise indicated, the article "a" or "an" if and as used herein is not intended to limit, and should not be construed as limiting, the description or a claim to a single element to which the article refers. Rather, the article "a" or "an" if and as used herein is intended to cover one or more such elements, unless the text expressly indicates otherwise.

Each and every patent, patent application and printed publication referred to above is incorporated herein by reference in toto to the fullest extent permitted as a matter of law.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. A catalytic complex of the formula:

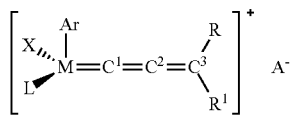

wherein either or both of $C^1$ and $C^2$ are optionally absent;
M is selected from the group consisting of Os and Ru;
R and $R^1$ are independently selected from the group consisting of hydrogen, $C_1$-$C_{20}$alkyl, and aryl, each R and $R^1$ optionally being substituted with $C_1$-$C_5$ alkyl, halogen, $C_1$-$C_{10}$ alkoxy, or phenyl group substituted with halogen, $C_1$-$C_5$ alkyl or $C_1$-$C_5$ alkoxy, or with a functional group;
X is an anionic ligand;
L is a nucleophilic carbine;
Ar is an $\eta^6$—$C_6H_6N$ or an alkyl substituted $C_6H_6$ring system; and
$A^{31}$ is an inorganic anion or an organic anion.

2. A method of performing ring closing metathesis, said method comprising contacting a diene with a catalytic complex of claim 1 under conditions appropriate, and for a time sufficient to produce a cyclic alkene.

3. A method of making catalytic complexes of claim 1 where both of $C^1$ and $C^2$ are present, said method comprising combining a precursor species of the formula

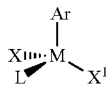

with a terminal acetylene, which can be substituted at the γ-position with alkyl or aryl groups, or optionally further substituted with alkyl or alkoxy groups of from 1 to 10 carbon atoms, or aryl groups, or functional groups of hydroxyl, thiol, thioether, ketone, aldehyde, ester, amide, amine, imine, nitro, carboxylic acid, disulfide, carbonate, isocyanate, carbodiimide, carboalkoxy, carbamate, and halogen,
and in the precursor species
M is selected from the group consisting of Os and Ru;
X and $X^1$ are anionic ligands;
L is a nucleophilic carbene; and
Ar is an $\eta^6$—$C_6H_6N$ or an alkyl substituted $C_6H_6$ring system.

4. A method as in claim 3 wherein the precursor species is formed from a dimer of the formula $[ArMXX^1]_2$ by exposing the dimer to a nucleophilic carbene in a suitable solvent.

5. A catalytic complex according to claim 1, wherein X is a halide.

6. A catalytic complex according to claim 5, wherein L is a nucleophilic carbene of the formula:

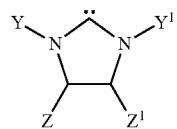 or 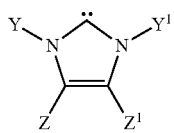

wherein
Y and $Y^1$ are independently selected from the group consisting of hydrogen, $C_1$-$C_{20}$ alkyl, $C_2$-$C_{20}$ C alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Y and $Y^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy; and Z and $Z^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Z and $Z^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy.

7. A catalytic complex according to claim 6, wherein the nucleophilic carbene is of the formula:

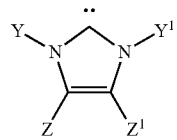

wherein
Y and $Y^1$ are independently selected from the group consisting of hydrogen, $C_1$-$C_{20}$ alkyl, $C_2$-$C_{20}$ C alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Y and $Y^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy; and Z and $Z^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Z and $Z^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy.

8. A catalytic complex according to claim 7, wherein Y and $Y^1$ are both 2,4,6-trimethylphenyl or both 2,6-diisopropylphenyl; and Z and $Z^1$ are both hydrogen.

9. A catalytic complex according to claim 1, wherein both of $C^1$ and $C^2$ are present; M is Ru; X is chloride; Ar is p-cymene; R and $R^1$ are both phenyl; $A^-$ is $PF_6^-$; and L is a nucleophilic carbene of the formula:

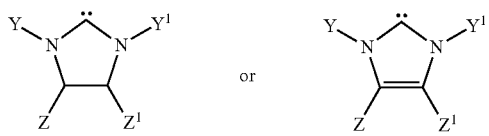 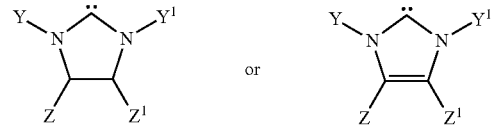

wherein

Y and Y$^1$ are independently selected from the group consisting of hydrogen, C$_1$-C$_{20}$ alkyl, C$_2$-C$_{20}$ C alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Y and Y$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy; and Z and Z$^1$ are independently selected from the group consisting of hydrogen, C$_1$-C$_{20}$ alkyl, C$_2$-C$_{20}$ alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Z and Z$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy.

10. A catalytic complex according to claim 9, wherein the nucleophilic carbene is of the formula:

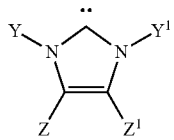

wherein

Y and Y$^1$ are independently selected from the group consisting of hydrogen, C$_1$-C$_{20}$ alkyl, C$_2$-C$_{20}$ C alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Y and Y$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy; and Z and Z$^1$ are independently selected from the group consisting of hydrogen, C$_1$-C$_{20}$ alkyl, C$_2$-C$_{20}$ alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Z and Z$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy.

11. A catalytic complex according to claim 10, wherein Y and Y$^1$ are both 2,4,6-trimethylphenyl or both 2,6-diisopropylphenyl; and Z and Z$^1$ are both hydrogen.

12. A method according to claim 2, wherein the cyclic alkene is disubstituted, trisubstituted, or tetrasubstituted.

13. A method according to claim 2, wherein both of C$^1$ and C$^2$ are present; M is Ru; X is chloride; Ar is p-cymene; R and R$^1$ are both phenyl; A$^{31}$ is PF$_6^{31}$; and L is a nucleophilic carbene of the formula:

wherein

Y and Y$^1$ are independently selected from the group consisting of hydrogen, C$_1$-C$_{20}$ alkyl, C$_2$-C$_{20}$ C alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Y and Y$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy; and Z and Z$^1$ are independently selected from the group consisting of hydrogen, C$_1$-C$_{20}$ alkyl, C$_2$-C$_{20}$ alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Z and Z$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy.

14. A method according to claim 13, wherein the nucleophilic carbene is of the formula:

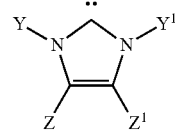

wherein

Y and Y$^1$ are independently selected from the group consisting of hydrogen, C$_1$-C$_{20}$ alkyl, C$_2$-C$_{20}$ C alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Y and Y$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy; and Z and Z$^1$ are independently selected from the group consisting of hydrogen, C$_1$-C$_{20}$ alkyl, C$_2$-C$_{20}$ alkenyl, C$_2$-C$_{20}$ alkynyl, C$_2$-C$_{20}$ alkoxycarbonyl, aryl, C$_1$-C$_{20}$ carboxylate, C$_1$-C$_{20}$ alkoxy, C$_2$-C$_{20}$ alkenyloxy, C$_2$-C$_{20}$ alkynyloxy, and aryloxy, each Z and Z$^1$ optionally being substituted with C$_1$-C$_5$ alkyl, halogen, C$_1$-C$_6$ alkoxy, or with a phenyl group substituted with halogen, C$_1$-C$_5$ alkyl or C$_1$-C$_5$ alkoxy.

15. A method according to claim 14, wherein Y and Y$^1$ are both 2,4,6-trimethylphenyl or both 2,6-diisopropylphenyl; and Z and Z$^1$ are both hydrogen.

16. A method according to claim 3, wherein the terminal acetylene is substituted at the γ-position with alkyl or aryl groups, or optionally further substituted with alkyl or alkoxy groups of from 1 to 10 carbon atoms, or aryl groups, or hydroxyl.

17. A method according to claim 16, wherein in the precursor species X and X$^1$ are both a halide.

18. A method according to claim 17, wherein in the precursor species L is a nucleophilic carbene of the formula:

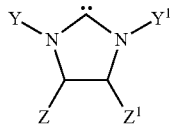 or 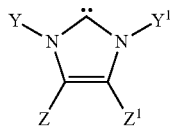

wherein

Y and $Y^1$ are independently selected from the group consisting of hydrogen, $C_1$-$C_{20}$ alkyl, $C_2$-$C_{20}$ C alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Y and $Y^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy; and Z and $Z^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Z and $Z^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy.

19. A method according to claim 18, wherein the nucleophilic carbene is of the formula:

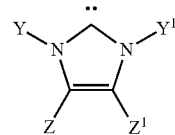

wherein

Y and $Y^1$ are independently selected from the group consisting of hydrogen, $C_1$-$C_{20}$ alkyl, $C_2$-$C_{20}$ C alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Y and $Y^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy; and Z and $Z^1$ are independently selected from the group consisting of hydrogen, $C_1$-$C_{20}$ alkyl, $C_2$-$C_{20}$ alkenyl, $C_2$-$C_{20}$ alkynyl, $C_2$-$C_{20}$ alkoxycarbonyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, and aryloxy, each Z and $Z^1$ optionally being substituted with $C_1$-$C_5$ alkyl, halogen, $C_1$-$C_6$ alkoxy, or with a phenyl group substituted with halogen, $C_1$-$C_5$ alkyl or $C_1$-$C_5$ alkoxy.

20. A method according to claim 19, wherein Y and $Y^1$ are both 2,4,6-trimethylphenyl or both 2,6-diisopropylphenyl; and Z and $Z^1$ are both hydrogen.

21. A method according to claim 4, wherein the dimer of the formula $[ArMXX^1]_2$ is $[(p\text{-cymene})\text{-RuCl}_2]_2$.

22. A method according to claim 2, wherein the catalytic complex is of claim 6.

* * * * *